(12) United States Patent
Stewart et al.

(10) Patent No.: US 6,927,322 B2
(45) Date of Patent: Aug. 9, 2005

(54) CABBAGE PROTEINASE INHIBITOR GENE CONFERS RESISTANCE AGAINST PLANT PESTS

(75) Inventors: C. Neal Stewart, Greensboro, NC (US); Roxanne M. Broadway, Grass Valley, CA (US)

(73) Assignees: Cornell Research Foundation, Inc., Ithaca, NY (US); University of North Carolina-Greensboro, Greensboro, NC (US)

( * ) Notice: Subject to any disclaimer, the term of this patent is extended or adjusted under 35 U.S.C. 154(b) by 55 days.

(21) Appl. No.: 09/822,080

(22) Filed: Mar. 30, 2001

(65) Prior Publication Data

US 2003/0018990 A1 Jan. 23, 2003

(51) Int. Cl.[7] .................. C12N 15/09; C12N 15/29; C12N 15/82; A01H 5/00; A01H 5/10
(52) U.S. Cl. ................... 800/302; 800/298; 800/295; 800/306; 800/278; 435/320.1; 435/69.1; 435/468
(58) Field of Search ................ 800/279, 278, 800/298, 302, 306, 295; 435/69.1, 419, 468, 320.1; 536/23.6, 24.1

(56) References Cited

U.S. PATENT DOCUMENTS

| | | | |
|---|---|---|---|
| 5,614,395 A | 3/1997 | Ryals et al. ............... | 435/172.3 |
| 5,623,054 A | 4/1997 | Zhang et al. ............... | 530/370 |
| 5,629,469 A | 5/1997 | Deluca-Flaherty et al. . | 800/205 |
| 5,640,804 A | 6/1997 | Driver et al. ................. | 47/58 |
| 5,650,505 A | 7/1997 | Ryals et al. ................. | 536/23.6 |

FOREIGN PATENT DOCUMENTS

| | | |
|---|---|---|
| EP | 0 298 918 A2 | 1/1989 |
| EP | 0 348 348 A2 | 12/1989 |
| EP | 0 693 554 A1 | 1/1996 |
| EP | 0 716 147 A2 | 6/1996 |
| EP | 0 651 813 B1 | 5/1998 |
| WO | WO 91/09060 | 6/1991 |

OTHER PUBLICATIONS

Broun et al. Science, vol. 282, pp. 131–133, 1998.*
Lazar et al. Molecular and Cellular Biology, vol. 8, No. 3, pp. 1247–1252, 1998.*
Laskowski et al. Ann. Rev. Biochem (1980), vol. 39, pp 593–626.*
Downing et al., "A *Brassica napus* Transcript Encoding a Protein Related to the Künitz Protease Inhibitor Family Accumulates Upon Water Stress in Leaves, Not in Seeds," *The Plant Journal* 2(5):685–693 (1992).
Urwin et al., "Resistance to Both Cyst and Root–Knot Nematodes Conferred by Transgenic *Arabidopsis* Expressing a Modified Plant Cystatin," *The Plant Journal* 12(2):455–461 (1997).
Broadway, "Tryptic Inhibitory Activity in Wild and Cultivated Crucifers," *Phytochemistry* 28(3):755–758 (1989).
Broadway et al., "Regulatory Mechanisms of Tryptic Inhibitory Activity in Cabbage Plants," *Phytochemistry* 29(12):3721–3725 (1990).
Broadway et al., "Influence of Cabbage Proteinase Inhibitors In Situ on the Growth of Larval *Trichoplusia ni* and *Pieris rapae*," *Journal of Chemical Ecology* 18(7):1009–1024 (1992).
Broadway, "Purification and Partial Characterization of Trypsin/Chymotrypsin Inhibitors From Cabbage Foliage," *Phytochemistry* 33(1):21–27 (1993).
Lorito et al., "Proteinase Inhibitors from Plants As a Novel Class of Fungicides," *MPMI* 7(4):525–527 (1994).
Broadway, "Are Insects Resistant to Plant Proteinase Inhibitors?," *J. Insect Physiol.* 41(2):107–116 (1995).

* cited by examiner

Primary Examiner—Medina A. Ibrahim
(74) Attorney, Agent, or Firm—Nixon Peabody LLP

(57) ABSTRACT

The present invention relates to a DNA construct containing a DNA for a serine proteinase inhibitor isolated from *Brassica oleracea*, which has antibiosis activity. The present invention also relates to transgenic plants and transgenic plant seeds containing that nucleic acid molecule. Resistance to herbivorous insects can be conferred to a plant by either transformation of the plant with the nucleic acid molecule which encodes a serine proteinase inhibitor isolated from *Brassica oleracea* or by application of that inhibitor to plants or plant seeds.

16 Claims, 7 Drawing Sheets

SEQUENCE LISTING

```
<160> NUMBER OF SEQ ID NOS: 12

<210> SEQ ID NO 1
<211> LENGTH: 809
<212> TYPE: DNA
<213> ORGANISM: Brassica oleracea
<220> FEATURE:
<221> NAME/KEY: source
<222> LOCATION: (1)..(809)
<223> OTHER INFORMATION: Serine proteinase inhibitor

<400> SEQUENCE: 1
gatgaatcct atgtttact tccttcttgc ctttaccact gttttggccg cgaccgcaaa      60
cgctggacca gttctcgaca ctgatggtga tatcatattc gacggcagtt actacgttct     120 cccctcatc tggggcccta caggtggcgg cctaactctc gtctcccgtc gtggcaacca     180
gtgtcccctc tttatcggac aggagcgttc agaggtcaac agggcattc ccgtgaaatt     240 ctcaaactgg aggtccagag ttgggttcgt ccccgaagaa gagaacctca acatcaagat     300
ggatgtcgaa cctacgatct gcgctcagtc agcttattgg tgggtcactc cagcccccag     360
tccctggagg tcgttgttca tagcggctgg tcctaagcca gaagctggag gagaagattc     420
gtcgaggagt ttcttccaga tcaagaaaac tgaagccaaa cttaacgctt acaagtttgt     480
attctgtagt gagggtaacg attgcatcga tgtcggtaaa aacgaggaag gtggcgttcg     540
gggtttggtt ttaggctcta cgccaccatt cgctaccca ttcgaggttg tgttcgtgaa     600
agctactggg acagacactt catccaagac tatgtctatt atctgagaga aattaaagac     660
cacttaataa agaggataag tgttataact tacctctaat aataaaactc tatctatgta     720
tgatgttttc tttgttcatc gatcatcatc atgtatggaa taaacatct ttcctttgtt     780 tctaaaaaaa aaaaaaaaa aaaaaaaa                                         809

<210> SEQ ID NO 2
<211> LENGTH: 214
<212> TYPE: PRT
<213> ORGANISM: Brassica oleracea
<220> FEATURE:
<221> NAME/KEY: PEPTIDE
<222> LOCATION: (1)..(214)
<223> OTHER INFORMATION: Serine proteinase inhibitor

<400> SEQUENCE: 2

Met Asn Pro Met Phe Tyr Phe Leu Leu Ala Phe Thr Thr Val Leu Ala
  1               5                  10                  15

Ala Thr Ala Asn Ala Gly Pro Val Leu Asp Thr Asp Gly Asp Ile Ile
```

```
                    20                  25                  30
Phe Asp Gly Ser Tyr Tyr Val Leu Pro Leu Ile Trp Gly Pro Thr Gly
        35                  40                  45

Gly Gly Leu Thr Leu Val Ser Arg Arg Gly Asn Gln Cys Pro Leu Phe
    50                  55                  60

Ile Gly Gln Glu Arg Ser Glu Val Asn Arg Gly Ile Pro Val Lys Phe
65                  70                  75                  80

Ser Asn Trp Arg Ser Arg Val Gly Phe Val Pro Glu Glu Asn Leu
                85                  90                  95

Asn Ile Lys Met Asp Val Glu Pro Thr Ile Cys Ala Gln Ser Ala Tyr
            100                 105                 110

Trp Trp Val Thr Pro Ala Pro Ser Pro Trp Arg Ser Leu Phe Ile Ala
            115                 120                 125

Ala Gly Pro Lys Pro Glu Ala Gly Gly Glu Asp Ser Ser Arg Ser Phe
            130                 135                 140

Phe Gln Ile Lys Lys Thr Glu Ala Lys Leu Asn Ala Tyr Lys Phe Val
145                 150                 155                 160

Phe Cys Ser Glu Gly Asn Asp Cys Ile Asp Val Gly Lys Asn Glu Glu
                165                 170                 175

Gly Gly Val Arg Gly Leu Val Leu Gly Ser Thr Pro Pro Phe Ala Thr
            180                 185                 190

Pro Phe Glu Val Val Phe Val Lys Ala Thr Gly Thr Asp Thr Ser Ser
            195                 200                 205

Lys Thr Met Ser Ile Ile
            210

<210> SEQ ID NO 3
<211> LENGTH: 216
<212> TYPE: PRT
<213> ORGANISM: G. max (soybean)
<220> FEATURE:
<221> NAME/KEY: PEPTIDE
<222> LOCATION: (1)..(216)
<223> OTHER INFORMATION: Kunitz-type trypsin inhibitor 3

<400> SEQUENCE: 3

Met Lys Ser Thr Ile Phe Phe Leu Phe Leu Phe Cys Ala Phe Thr Thr
1               5                   10                  15

Ser Tyr Leu Pro Ser Ala Ile Ala Asp Phe Val Leu Asp Asn Glu Gly
                20                  25                  30

Asn Pro Leu Glu Asn Gly Gly Thr Tyr Tyr Ile Leu Ser Asp Ile Thr
            35                  40                  45

Ala Phe Gly Gly Ile Arg Ala Ala Pro Thr Gly Asn Glu Arg Cys Pro
        50                  55                  60

Leu Thr Val Val Gln Ser Arg Asn Glu Leu Asp Lys Gly Ile Gly Thr
65                  70                  75                  80

Ile Ile Ser Ser Pro Tyr Arg Ile Arg Phe Ile Ala Glu Gly His Pro
                85                  90                  95

Leu Ser Leu Lys Phe Asp Ser Phe Ala Val Ile Met Leu Cys Val Gly
            100                 105                 110

Ile Pro Thr Glu Trp Ser Val Val Glu Asp Leu Pro Glu Gly Pro Ala
            115                 120                 125

Val Lys Ile Gly Glu Asn Lys Asp Ala Met Asp Gly Trp Phe Arg Leu
            130                 135                 140

Glu Arg Val Ser Asp Asp Glu Phe Asn Asn Tyr Lys Leu Val Phe Cys
145                 150                 155                 160
```

```
Pro Gln Gln Ala Glu Asp Asp Lys Cys Gly Asp Ile Gly Ile Ser Ile
                165                 170                 175

Asp His Asp Asp Gly Thr Arg Arg Leu Val Val Ser Lys Asn Lys Pro
            180                 185                 190

Leu Val Val Gln Phe Gln Lys Leu Asp Lys Glu Ser Leu Ala Lys Lys
        195                 200                 205

Asn His Gly Leu Ser Arg Ser Glu
    210                 215

<210> SEQ ID NO 4
<211> LENGTH: 218
<212> TYPE: PRT
<213> ORGANISM: Brassica napus
<220> FEATURE:
<221> NAME/KEY: PEPTIDE
<222> LOCATION: (1)..(218)
<223> OTHER INFORMATION: BnD22 drought-induced proteinase inhibitor

<400> SEQUENCE: 4

Met Lys Thr Phe Phe Leu Val Thr Leu Leu Ala Ala Ala Val Cys
 1               5                  10                  15

Thr His Gly Arg Glu Gln Val Lys Asp Ser Asn Gly Asn Pro Val Lys
            20                  25                  30

Arg Gly Ala Lys Tyr Phe Ile Gln Pro Ala Lys Ser Asn Ala Gly Gly
        35                  40                  45

Leu Val Pro Ala Ala Ile Asn Leu Leu Pro Phe Cys Pro Leu Gly Ile
    50                  55                  60

Thr Gln Thr Leu Leu Pro Tyr Gln Pro Gly Leu Pro Val Ser Phe Gly
65                  70                  75                  80

Tyr Glu Pro Val Ile Val Gly Thr Asp Tyr Ile Tyr Thr Ser Thr Thr
                85                  90                  95

Ile Asn Ile Glu Phe Glu Ser Asp Ile Trp Pro Val Cys Asn Glu Leu
            100                 105                 110

Ser Lys Leu Trp Ala Val Asp Val Ser Ser Ala Ala Lys Glu Pro
        115                 120                 125

Ala Ile Ile Ile Gly Gly Glu Ser Thr Ala Pro Asn Ser Leu Phe Lys
    130                 135                 140

Ile Glu Glu Ala Thr Glu Ala Asn Thr Tyr Lys Leu Thr Thr Ser Tyr
145                 150                 155                 160

Gly Thr Val Gly Thr Ile Pro Gly Pro Trp Leu Ser Ala Pro Gln Leu
                165                 170                 175

Ile Val Thr Asn Asp Glu Ser Lys Thr Leu Phe Val Lys Phe Val Lys
            180                 185                 190

Val Asp Asp Ala Ala Thr Lys Ala Thr Thr Ser Thr Ser Arg Val Glu
        195                 200                 205

Lys Leu Gly Leu Lys Met Phe Pro Phe Tyr
    210                 215

<210> SEQ ID NO 5
<211> LENGTH: 17
<212> TYPE: PRT
<213> ORGANISM: Brassica oleracea
<220> FEATURE:
<221> NAME/KEY: PEPTIDE
<222> LOCATION: (1)..(17)
<223> OTHER INFORMATION: BoPI peptide

<400> SEQUENCE: 5
```

```
Val Leu Asp Thr Asp Gly Asp Ile Ile Phe Asp Gly Ser Tyr Tyr Val
 1               5                  10                 15

Leu
```

```
<210> SEQ ID NO 6
<211> LENGTH: 37
<212> TYPE: PRT
<213> ORGANISM: Artificial Sequence
<220> FEATURE:
<223> OTHER INFORMATION: Description of Artificial Sequence:  Kunitz
      inhibitor family amino-terminal conserved region
<221> NAME/KEY: PEPTIDE
<222> LOCATION: (1)..(37)
<223> OTHER INFORMATION: Xaa at positions 5, 7, 22, 27-31 and 33 is any
      amino acid

<400> SEQUENCE: 6

Leu Ile Val Asp Xaa Asp Xaa Glu Asp Asn Thr Tyr Asp Gly Arg Lys
 1               5                  10                 15

His Asp Glu Asn Gln Xaa Leu Ile Val Met Xaa Xaa Xaa Xaa Xaa Tyr
            20                  25                  30

Xaa Leu Ile Val Met
        35
```

```
<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
ggcagttact acgttctccc c                                              21
```

```
<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
cgataggggt agcgaatg                                                  18
```

```
<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
acgaccaatt tacagcccag                                                20
```

```
<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
```

-continued

```
gttgtacaaa cgcttccctc agc                                            23

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
atttggggaa tctttggtcc                                                20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
acagtacgga ttgggtagcg                                                20
```

CABBAGE PROTEINASE INHIBITOR GENE CONFERS RESISTANCE AGAINST PLANT PESTS

This invention was developed with government funding by NRI Grant 91-37302-6219. The U.S. Government may have certain rights.

FIELD OF THE INVENTION

This invention relates to a DNA construct which contains one or more nucleic acid molecules encoding a serine proteinase inhibitor isolated from Brassica oleracea which has antibiosis activity, and methods of conferring resistance to plants to herbivorous insects by transforming plants with such DNA constructs, and transgenic plants and seeds transformed with such nucleic acid constructs.

BACKGROUND OF THE INVENTION

Plant genes that protect against herbivorous insects may be useful for heterologous expression in food and fiber crops (Boulter, "Genetic Engineering of Plants for Insect Resistance," Outlook on Agriculture 18:2–6 (1989); Vogel et al., "Natural Proteinase Inhibitors," Academic Press, New York (1968)). Proteinase inhibitors (PIs) are common in plants and have drawn attention as possible transgenes for insect defense in crops. PIs are of particular interest because they are generally the product of a single gene, and inhibit proteolytic enzymes of animal and fungal origin, but rarely plant origin, and therefore are thought to act as protective agents (Baldwin et al., "Rapid Changes in Tree Leaf Chemistry Induced by Damage: Evidence for Communication Between Plants," Science 221:277–279 (1983); Brattsten, "Bioengineering of Crop Plants and Resistant Biotype Evolution in Insects: Counteracting Coevolution," Archives of Insect Biochemistry and Physiology 17:253–267 (1991); Green et al., "Wound-Induced Proteinase Inhibitor in Plant Leaves: A Possible Defense Mechanism Against Insects," Science 175:776–777 (1972); Hilder et al., "Transgenic Plants Conferring Insect Tolerance: Protease Inhibitor Approach," in Kung, eds., Transpenic Plants, London: Academic Press, Inc., pp.317–338 (1993); Laskowski et al., "The Enzymes," Academic Press, Inc., New York (1977)). Several studies have demonstrated that PIs might provide adequate protection against a variety of economically important lepidopteran insects (Broadway et al., "The Effect of Dietary Protein on the Growth and Digestive Physiology of Larval Heliocoverpa zea and Spodoptera exiqua," J. Insect Physiol. 32:827–833 (1986); Hoy et al., "Feeding Response of Artogeia rapae (Lepidoptera:Pieridae) and Trichoplusia ni (Lepidoptera:Noctuidae) to Cabbage Leaf Age," Environ. Entomol. 16:680–682 (1987); Johnson et al., "Expression of Proteinase Inhibitors I and II in Transgenic Tobacco Plants: Effect on Natural Defense Against Manduca sexta Larvae," Proc. Natl. Acad. Sci. USA 86:9871–9875 (1989); Lipke et al., "Effect of Soybean Inhibitors on Growth of Tribolium confusum," A Food Chem 2:410–414 (1954); Oppert et al., "Dietary Mixtures of Cysteine and Serine Proteinase Inhibitors Exhibit Synergistic Toxicity Toward the Red Flour Beetle, Tribolium Castaneum," Comp. Biochem. Physiol. 105C:379–385 (1993); Sánchez-Serrano et al., "Wound-Induced Expression of a Potato Proteinase Inhibitor II Gene in Transgenic Tobacco Plants," EMBO J. 6:303–306 (1987); Thomas et al., "Protease Inhibitors of Manduca Sexta Expressed in Transgenic Cotton," Plant Cell Reports 14:758–762 (1995); Thomas et al., "Introduction and Expression of an Insect Proteinase Inhibitor in Alfalfa (Medicago sativa L.)," Plant Cell Reports 14:31–36 (1994); Xu et al., "Constitutive Expression of a Cowpea Trypsin Inhibitor Gene, CpTi, in Transgenic Rice Plants Confers Resistance to Two Major Rice Pests," Molecular Breeding 2:167–173 (1996)).

The production and accumulation of PIs in plants can be activated by a variety of mechanisms. Potato, tomato and poplar PIs have been shown to be wound inducible, both at the site of wounding and systemically (Bradshaw et al., "Systemically Wound-Responsive Genes in Poplar Trees Encode Proteins Similar to Sweet Potato Sporamins and Legume Kunitz Trypsin Inhibitor," Plant Mol. Biol. 14:51–59 (1990); Graham et al., "Regulation of Synthesis of Proteinase Inhibitors I and II mRNAs in Leaves of Wounded Tomato Plants," Planta 169:399–405 (1986); Sánchez-Serrano et al., "Nucleotide Sequence of Proteinase Inhibitor II Encoding cDNA of Potato (Solanum Tuberosum) and Its Mode of Expression," Mol. Gen. Genet. 203:15–20 (1986)). In contrast, the production of PIs in cabbage (Brassica oleracea), especially trypsin and chymotrypsin inhibitors, are linked to plant development (Broadway et al., "Regulatory Mechanisms of Tryptic Inhibitory Activity in Cabbage Plants," Phytochem. 29:3721–3725 (1990)). Low levels of PI activity in cabbage are produced in young foliage in seedlings (Broadway et al., "Regulatory Mechanisms of Tryptic Inhibitory Activity in Cabbage Plants," Phytochem. 29:3721–3725 (1990); Broadway et al., "Influence of Cabbage Proteinase Inhibitors in situ on the Growth of Larval Trichoplusia ni and Pieris rapae," J. Chemical Ecology 18:1009–1023 (1992). When the plant reaches the 11–13 leaf stage, the level of PI activity gradually increases in young leaves, and reaches a maximal level of activity in the young foliage on mature plants. The production of PIs in cabbage is synchronized with the appearance of herbivorous insects in the field. Thus, the PIs are present when the resistance factor is most needed against these pests (Broadway et al., "Regulatory Mechanisms of Tryptic Inhibitory Activity in Cabbage Plants," Phytochem. 29:3721–3725 (1990); Broadway et al., "Influence of Cabbage Proteinase Inhibitors in situ on the Growth of Larval Trichoplusia ni and Pieris rapae," J.Chem. Ecol. 18:1009–1023 (1992)). In addition, cabbage foliar extracts containing PIs have been shown to significantly reduced growth and development of larval Lepidoptera and plant pathogenic fungi (Broadway, "Are Insects Resistant to Plant Proteinase Inhibitors?" J. Insect Physiol. 41:107–116 (1995); Broadway et al., "Influence of Cabbage Proteinase Inhibitors in situ on the Growth of Larval Trichoplusia ni and Pieris rapae," J. Chem. Ecol. 18:1009–1023 (1992); Lorito et al., "Proteinase Inhibitors from Plants as a Novel Class of Fungicides," Mol. Plant-Microbe Interact. 4:525–527 (1994)).

Genetic engineering of plants, which entails the isolation and manipulation of genetic material (usually in the form of DNA or RNA), and the subsequent introduction of that genetic material into plants or plant cells, offers considerable promise as a tool for the control of plant pests. If transgenic plants can be developed which express naturally occurring pest inhibitors, the need for expensive and potentially harmful chemical pest control measures is reduced. What is needed is a method of providing, and/or enhancing protection against herbivorous insects through the expression of the cabbage PI in crop plants.

The present invention is directed to overcoming these and other deficiencies in the art.

SUMMARY OF THE INVENTION

The present invention relates to a DNA construct which contains one or more nucleic acid molecules encoding a serine protease inhibitor isolated from *Brassica oleracea* which has antibiosis activity. The nucleic acid molecule of the construct is operably linked to a heterologous DNA promoter and a 3' regulatory region.

The present invention also relates to a method of conferring resistance to insects to plants. This involves transforming a plant or plant seed with a DNA construct containing a nucleic acid molecule isolated from *Brassica oleracea* which encodes for a serine proteinase inhibitor having insect antibiosis activity, and growing the transgenic plant or plant seed under conditions to impart resistance to insects.

This invention also relates to transgenic plants transformed with a nucleic acid construct which contains one or more nucleic acid molecules encoding a serine protease inhibitor isolated from *Brassica oleracea* which has antibiosis activity.

The present invention provides a highly specific tool for the expression of a heterologous nucleic acid in plants which imparts increased protection against herbivores insects, thereby overcoming existing deficiencies in plant pest control.

DETAILED DESCRIPTION OF THE INVENTION

Figure 1:
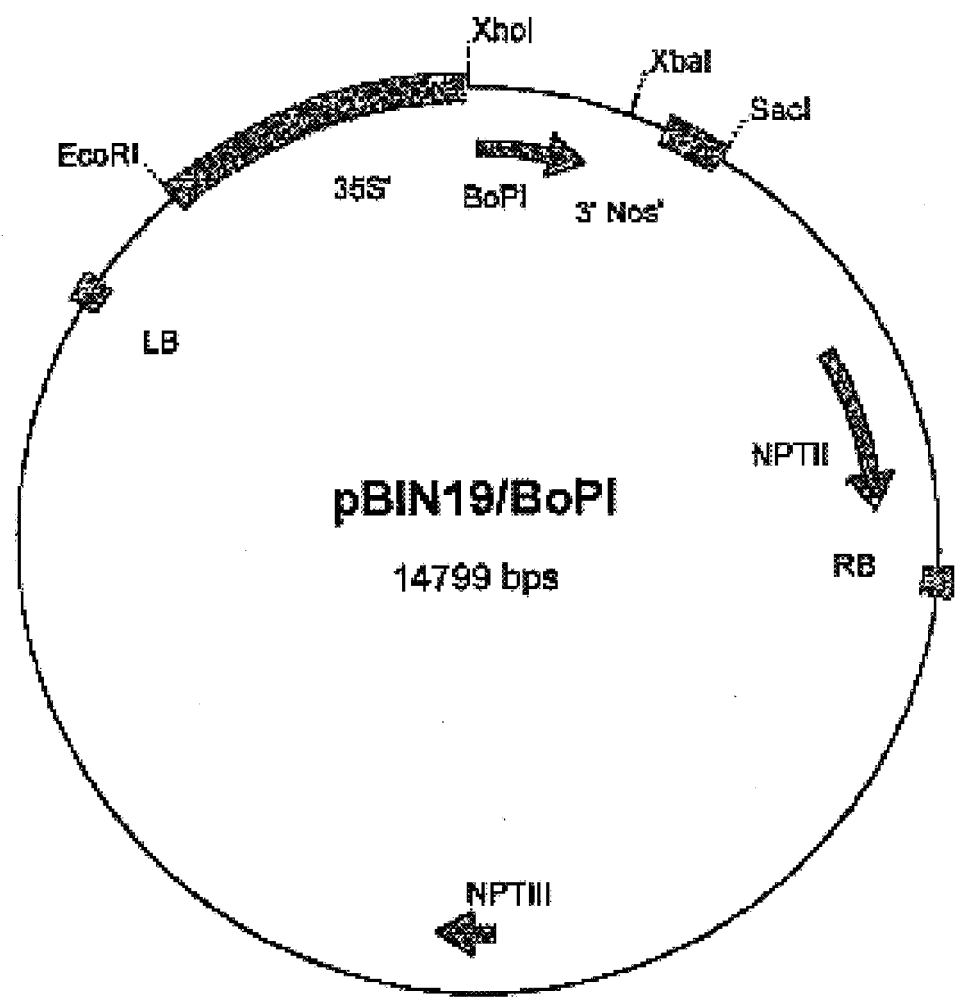
FIG. 1 is a plasmid map of pBIN/BoPI, showing the *Brassica oleracea* proteinase inhibitor cDNA (bopi) inserted into the plant expression vector pBIN19.

The present invention relates to a DNA construct which contains one or more nucleic acid molecules encoding a serine proteinase inhibitor isolated from *Brassica oleracea* which has antibiosis activity. An example of a nucleic acid suitable for use in the present invention is isolated from *Brassica oleracea*, and has a nucleotide sequence corresponding to SEQ. ID No. 1, as follows:

```
gatgaatcct atgttttact tccttcttgc ctttaccact gttttggccg cgaccgcaaa   60
cgctggacca gttctcgaca ctgatggtga tatcatattc gacggcagtt actacgttct  120
ccccctcatc tggggcccta caggtggcgg cctaactctc gtctcccgtc gtggcaacca  180
gtgtcccctc tttatcggac aggagcgttc agaggtcaac agggcattc ccgtgaaatt   240 ctcaaactgg aggtccagag ttgggttcgt ccccgaagaa gagaacctca acatcaagat  300
ggatgtcgaa cctacgatct gcgctcagtc agcttattgg tgggtcactc cagccccag   360 tccctggagg tcgttgttca tagcggctgg tcctaagcca gaagctggag gagaagattc  420
gtcgaggagt ttcttccaga tcaagaaaac tgaagcaaa cttaacgctt acaagtttgt  480
attctgtagt gagggtaacg attgcatcga tgtcggtaaa aacgaggaag gtggcgttcg  540
gggtttggtt ttaggctcta cgccaccatt cgctacccca ttcgaggttg tgttcgtgaa  600
agctactggg acagacactt catccaagac tatgtctatt atctgagaga aattaaagac  660
cacttaataa agaggataag tgttataact tacctctaat aataaaactc tatctatgta  720
tgatgttttc tttgttcatc gatcatcatc atgtatggaa taaacatct ttcctttgtt   780 tctaaaaaaa aaaaaaaaa aaaaaaaaa                                     809
```

An examnple of a serine proteinase inhibitor suitable for use in the present invention is the serine proteinase inhibitor encoded by SEQ. ID. No. 1, having an amino acid sequence of SEQ. ID. No. 2 as follows:

```
Met Asn Pro Met Phe Tyr Phe Leu Leu Ala Phe Thr Thr Val Leu Ala
 1               5                  10                  15
Ala Thr Ala Asn Ala Gly Pro Val Leu Asp Thr Asp Gly Asp Ile Ile
            20                  25                  30
Phe Asp Gly Ser Tyr Tyr Val Leu Pro Leu Ile Trp Gly Pro Thr Gly
        35                  40                  45
Gly Gly Leu Thr Leu Val Ser Arg Arg Gly Asn Gln Cys Pro Leu Phe
    50                  55                  60
Ile Gly Gln Glu Arg Ser Glu Val Asn Arg Gly Ile Pro Val Lys Phe
65                  70                  75                  80
Ser Asn Trp Arg Ser Arg Val Gly Phe Val Pro Glu Glu Asn Leu
                85                  90                  95
Asn Ile Lys Met Asp Val Glu Pro Thr Ile Cys Ala Gln Ser Ala Tyr
            100                 105                 110
Trp Trp Val Thr Pro Ala Pro Ser Pro Trp Arg Ser Leu Phe Ile Ala
            115                 120                 125
Ala Gly Pro Lys Pro Glu Ala Gly Gly Glu Asp Ser Ser Arg Ser Phe
        130                 135                 140
Phe Gln Ile Lys Lys Thr Glu Ala Lys Leu Asn Ala Tyr Lys Phe Val
145                 150                 155                 160
Phe Cys Ser Glu Gly Asn Asp Cys Ile Asp Val Gly Lys Asn Glu Glu
                165                 170                 175
Gly Gly Val Arg Gly Leu Val Leu Gly Ser Thr Pro Pro Phe Ala Thr
            180                 185                 190
Pro Phe Glu Val Val Phe Val Lys Ala Thr Gly Thr Asp Thr Ser Ser
        195                 200                 205
Lys Thr Met Ser Ile Ile
    210
```

This protein has a molecular weight of 21 kDa (as determined by sodium dodecyl sulfate polyacrylamide gel electrophoresis after the protein was prepared under reducing conditions, on direct comparison to migration of 21 kDa protein) and an isoelectric point of 4.94 (determined by isoelectric focusing electrophoresis from a regression of distance versus isoelectric point of standard proteins).

Fragments of the above protein and its encoding nucleic acid are also encompassed by the present invention. Suitable fragments can be produced by several means. In the first, subclones of the gene encoding the protein of the present invention are produced by conventional molecular genetic manipulation by subcloning gene fragments. The subclones then are expressed in vitro or in vivo in bacterial cells to yield a smaller protein or peptide.

In another approach, based on knowledge of the primary structure of the protein of the present invention, fragments of the gene of the present invention may be synthesized by using the PCR technique together with specific sets of primers chosen to represent particular portions of the protein. These then would be cloned into an appropriate vector for increased expression of an accessory peptide or protein.

Chemical synthesis can also be used to make suitable fragments. Such a synthesis is carried out using known amino acid sequences for the protein of the present invention. These fragments can then be separated by conventional procedures (e.g., column chromatography, gel electrophoresis) and used in the methods of the present invention.

Variants may also (or alternatively) be prepared by, for example, the deletion or addition of amino acids that have minimal influence on the properties, secondary structure, and hydropathic nature of the polypeptide. For example, a polypeptide may be conjugated to a signal (or leader)

sequence at the N-terminal end of the protein which co-translationally or post-translationally directs transfer of the protein. The polypeptide may also be conjugated to a linker or other sequence for ease of synthesis, purification, or identification of the polypeptide.

Suitable DNA molecules useful in the present invention also include those that hybridize to a DNA molecule comprising a nucleotide sequence of SEQ. ID. No. 1 under stringent conditions. An example of suitable stringency conditions is when hybridization is carried out at a temperature of 56° C. for 20 hours in a buffer containing 0.9M NaCl, 50 mM Tris-HCl, pH 7.4, 10 mM EDTA, 0.1% sodium dodecyl sulfate, 0.2% ficoll, 0.2% polyvinylpyrrolidone, 0.2% bovine serum albumin, 50 µm g/ml E. coli DNA. Less stringent hybridization conditions may be carried out using the hybridization buffer described above, at a temperature of 45° C., or in aqueous buffer without blocking agents at a temperature of 65° C.

The nucleic acid molecule encoding a serine proteinase inhibitor of the present invention can be incorporated in cells using conventional recombinant DNA technology. Generally, this involves inserting the nucleic acid molecule into an expression system to which the nucleic acid molecule is heterologous (i.e., not normally present). The heterologous nucleic acid molecule is inserted into the expression system or vector in proper sense orientation and correct reading frame. The vector contains the necessary elements for the transcription and translation of the inserted protein-coding sequences.

The nucleic acid molecule of the present invention may be inserted into any of the many available expression vectors and cell systems using reagents that are well known in the art. In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTI, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens*. Fraley, et al., "Expression of Bacterial Genes in Plant Cells," *Proc. Nat'l Acad. Sci.*, 80:48034807 (1983), which is hereby incorporated by reference in its entirety.

Further improvement of this technique led to the development of the binary vector system. Bevan, M., *"Binary Agrobacterium* Vectors for Plant Transformation," *Nucleic Acids Res.* 12:8711–8721 (1984), which is hereby incorporated by reference in its entirety. In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly used vector is pBin19 (Frisch, et al., "Complete Sequence of the Binary Vector Bin19," *Plant Molec. Biol.* 27:405–409 (1995), which is hereby incorporated by reference in its entirety). Any appropriate vectors now known or later described for genetic transformation are suitable for use with the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

In one aspect of the present invention, the nucleic acid molecule of the present invention is incorporated into an appropriate vector in the sense direction, such that the open reading frame is properly oriented for the expression of the encoded protein under control of a promoter of choice.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism. Examples of some constitutive promoters that are widely used for inducing expression of transgenes include the nopoline synthase (NOS) gene promoter, from *Agrobacterium tumefaciens*, (U.S. Pat. No. 5,034,322 to Rogers et al., which is hereby incorporated by reference in its entirety), the cauliflower mosaic virus (CaMv) 35S and 19S promoters (U.S. Pat. No. 5,352,605 to Fraley et al., which is hereby incorporated by reference in its entirety), those derived from any of the several actin genes, which are known to be expressed in most cells types (U.S. Pat. No. 6,002,068 to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter for use in the present invention is a glucocorticoid-inducible promoter (Schena et al., "A Steroid-Inducible Gene Expression System for Plant Cells," *Proc. Natl. Acad. Sci.* 88:10421–5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog (Schena et al., "A Steroid-Inducible Gene Expression System for Plant Cells," *Proc. Natl. Acad. Sci. USA* 88:10421-5 (1991); Aoyama et al., "A Glucocorticoid-Mediated Transcriptional Induction System in Transgenic Plants," *Plant J.* 11: 605–612 (1997), and McNellis et al., "Glucocorticoid-Inducible Expression of a Bacterial Avirulence Gene in Transgenic Arabidopsis Induces Hypersensitive Cell Death, *Plant J.* 14(2):247–57 (1998), which are hereby incorporated by reference in its entirety). In addition, inducible promoters include promoters that function in a tissue specific manner to regulate the gene of interest within selected tissues of the plant. Examples of such tissue specific promoters include seed, flower, or root specific promoters as are well known in the field (U.S. Pat. No. 5,750,385 to Shewmaker et al., which is hereby incorporated by reference in its entirety). In the preferred embodiment of the present invention, a heterologous promoter is linked to the nucleic acid of the construct, where "heterologous promoter" is defined as a promoter to which the nucleic acid of the construct is not linked in nature.

The DNA construct of the present invention also includes an operable 3' regulatory region, selected from among those which are capable of providing correct transcription termination and polyadenylation of mRNA for expression in the host cell of choice, operably linked to a DNA molecule which encodes for a protein of choice. A number of 3' regulatory regions are known to be operable in plants. Exemplary 3' regulatory regions include, without limitation, the nopaline synthase ("nos") 3' regulatory region (Fraley, et al., "Expression of Bacterial Genes in Plant Cells," *Proc. Nat'l Acad. Sci. USA* 80:4803–4807 (1983), which is hereby incorporated by reference in its entirety) and the cauliflower mosaic virus ("CaMV") 3' regulatory region (Odell, et al., "Identification of DNA Sequences Required for Activity of the Cauliflower Mosaic Virus 35S Promoter," *Nature* 313 (6005):810–812 (1985), which is hereby incorporated by reference in its entirety). Virtually any 3' regulatory region known to be operable in plants would suffice for proper expression of the coding sequence of the nucleic acid of the present invention.

The vector of choice, promoter, and an appropriate 3' regulatory region can be ligated together to produce the plasmid of the present invention using well known molecular cloning techniques as described in Sambrook et al., *Molecular Cloning: A Laboratory Manual*, Second Edition, Cold Spring Harbor Press, N.Y. (1989), and Ausubel, F. M. et al. (1989) *Current Protocols in Molecular Biology*, John Wiley & Sons, New York, N.Y., which are hereby incorporated by reference in its entirety.

Once the DNA construct of the present invention has been prepared, it is ready to be incorporated into a host cell. Recombinant molecules can be introduced into cells via transformation, particularly transduction, conjugation, mobilization, or electroporation. The DNA sequences are cloned into the host cell using standard cloning procedures known in the art, such as those described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like. Preferably the host cells are either a bacterial cell or a plant cell.

One approach to transforming plant cells with a DNA construct in order to carry out the method of the present invention is particle bombardment (also known as biolistic transformation) of the host cell. This can be accomplished in one of several ways. The first technique is disclosed in U.S. Pat. Nos. 4,945,050, 5,036,006, and 5,100,792, all to Sanford, et al., which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Transient expression in protoplasts allows quantitative studies of gene expression since the population of cells is very high (on the order of $10^6$). To deliver DNA inside protoplasts, several methodologies have been proposed, but the most common are electroporation (Fromm et al., "Expression of Genes Transferred Into Monocot and Dicot Plants by Electroporation," *Proc. Natl. Acad. Sci. USA* 82:5824–5828 (1985), which is hereby incorporated by reference in its entirety) and polyethylene glycol (PEG) mediated DNA uptake (Krens et al., "In Vitro Transformation of Plant Protoplasts with Ti-Plasmid DNA," *Nature* 296:72–74 (1982), which is hereby incorporated by reference in its entirety). During electroporation, the DNA is introduced into the cell by means of a reversible change in the permeability of the cell membrane due to exposure to an electric field. PEG transformation introduces the DNA by changing the elasticity of the membranes. Unlike electroporation, PEG transformation does not require any special equipment and transformation efficiencies can be equally high. Another appropriate method of introducing the gene construct of the present invention into a host cell is fusion of protoplasts with other entities, either minicells, cells, lysosomes, or other fusible lipid-surfaced bodies that contain the chimeric gene (Fraley, et al., "Entrapment of a Bacterial Plasmid in Phospholipid Vesicles: Potential for Gene Transfer," *Proc. Natl. Acad. Sci. USA*, 76:3348–52 (1979), which is hereby incorporated by reference in its entirety).

Stable transformants are preferable for the methods of the present invention. An appropriate method of stably introducing the DNA construct into plant cells is to infect a plant cell with *Agrobacterium tumefaciens* or *Agrobacterium rhizogenes* previously transformed with the DNA construct. Under appropriate conditions known in the art, the transformed plant cells are grown to form shoots or roots, and develop further into plants.

Plant tissues suitable for transformation include, but are not limited to, floral buds, leaf tissue, root tissue, meristems, zygotic and somatic embryos, megaspores, and anthers.

After transformation, the transformed plant cells can be selected and regenerated. Preferably, transformed cells are first identified using a selection marker simultaneously introduced into the host cells along with the DNA construct of the present invention. The most widely used reporter gene for gene fusion experiments has been uidA, a gene from

*Escherichia coli* that encodes the β-glucuronidase protein, also known as GUS (Jefferson et al., "GUS Fusions: βGlucuronidase as a Sensitive and Versatile Gene Fusion Marker in Higher Plants," *EMBO J.* 6:3901–3907 (1987), which is hereby incorporated by reference in its entirety). Other suitable selection markers include, without limitation, markers encoding for antibiotic resistance, such as the nptII gene which confers kanamycin resistance (Fraley, et al., *Proc. Natl. Acad. Sci. USA*, 80:4803–4807 (1983), which is hereby incorporated by reference in its entirety) and the dhfr gene, which confers resistance to methotrexate (Bourouis et al., *EMBO J.* 2:1099–1104 (1983), which is hereby incorporated by reference in its entirety). A number of antibiotic-resistance markers are known in the art and others are continually being identified. Any known antibiotic-resistance marker can be used to transform and select transformed host cells in accordance with the present invention. Cells or tissues are grown on a selection medium containing an antibiotic, whereby generally only those transformants expressing the antibiotic resistance marker continue to grow. Similarly, enzymes providing for production of a compound identifiable by luminescence, such as luciferase, are useful. The selection marker employed will depend on the target species; for certain target species, different antibiotics, herbicide, or biosynthesis selection markers are preferred.

Once a recombinant plant cell or tissue has been obtained, it is possible to regenerate a full-grown plant therefrom. Means for regeneration vary from species to species of plant, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

Plant regeneration from cultured protoplasts is described in Evans, et al., *Handbook of Plant Cell Cultures, Vol. 1*: (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference in its entirety.

After the DNA construct is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field. Alternatively, transgenic seeds are recovered from the transgenic plants. The seeds can then be planted in the soil and cultivated using conventional procedures to produce transgenic plants.

Confirmation of the presence of the transgene in transformed plants can be made by any of the methods for DNA analysis known to those skilled in the art, including PCR and Southern blotting. Expression of BoPI, and the degree of insect antibiosis exhibited by the transgenic plants can be measured using standard assays known to those of ordinary skill in the art, and described in further detail in the Examples below.

The present invention also relates to a method of imparting a factor to plants that confers resistance to herbivorous insects. This involves transforming plants with the construct of the present invention, using methods such as described above, and regenerating the plant under conditions to impart resistance.

The present invention also relates to transgenic plants or plant seeds, transformed with the nucleic acid of the present invention under conditions effective to yield transcription of the DNA molecule in the plant cell, and regenerating the transformed plant to full grown as described above.

Alternatively, transgenic seeds are recovered from the transgenic plants. The seeds can then be planted in the soil and cultivated using conventional procedures to produce transgenic plants.

Just as the increased expression of chitinolytic genes confers resistance to transgenic plants harboring one or more gene(s) encoding for BoPI, relative to wild-type (non-transgenic) plants (see Examples, below), resulting in the expression of the serine proteinase inhibitor, direct exposure of a plant to the serine proteinase inhibitor of the present invention can be expected to increase the resistance of treated plants to harm from insect pests. Accordingly, the present invention also relates to a method conferring resistance against insects to plants by the direct application of a serine proteinase inhibitor, isolated from *Brassica oleracea*. This method involves applying a serine proteinase inhibitor of the present invention to all or part of a plant or a plant seed under conditions effective to confer resistance against insects to the plants so treated.

The method of the present invention involving application of a serine proteinase inhibitor can be carried out through a variety of procedures when all or part of the plant is treated, including leaves, stems, roots, etc. This may (but need not) involve infiltration of the serine proteinase inhibitor into the plant.

Suitable application methods include topical application (e.g., high or low pressure spraying), injection, and leaf abrasion proximate to when application of the serine proteinase inhibitor takes place. When treating plant seeds, in accordance with the application embodiment of the present invention, a serine proteinase inhibitor can be applied by low or high pressure spraying, coating, immersion, or injection. Other suitable application procedures can be envisioned by those skilled in the art provided they are able to effect contact of the serine proteinase inhibitor with the plant or plant seed. Once treated with a serine proteinase inhibitor of the present invention, the seeds can be planted in natural or artificial soil and cultivated using conventional procedures to produce plants.

The methods of the present invention can be utilized to confer resistance upon a wide variety of plants, including but not limited to, monocots such as Gramineae (e.g., grass, corn, grains, bamboo, sugar cane), Liliaceae (e.g., onion, garlic, asparagus, tulips, hyacinths, day lily, and aloes), Iridaceae (e.g., iris, gladioli, freesia, crocus, and watsonia), and Orchidacea (e.g., orchid), and dicots including Salicaceae (e.g., willow, and poplar), Ranunculaceae (e.g., Delphinium, Paeonia, Ranunculus, Anemone, Clematis, columbine, and marsh marigold), Magnoliaceae (e.g., tulip tree and Magnolia), Cruciferae (e.g., mustards, cabbage, cauliflower, broccoli, brussel sprouts, kale, kohlrabi, turnip, and radish), Rosaceae (e.g., strawberry, blackberry, peach, apple, pear, quince, cherry, almond, plum, apricot, and rose), Leguminosae (e.g., pea, bean, peanut, alfalfa, clover, vetch, redbud, broom, wisteria, lupine, black locust, and acacia), Malvaceae (e.g., cotton, okra, and mallow), Umbelliferae (e.g., carrot, parsley, parsnips, and hemlock), Labiatae (e.g., mint, peppermints, spearmint, thyme, sage, and lavender), Solanaceae (e.g., potato, tomato, pepper, eggplant, and Petunia), Cucurbitaceae (e.g., melon, squash, pumpkin, and cucumber), Compositae (e.g., sunflower, endive, artichoke, lettuce, safflower, aster, marigold, dandelions, sage brush, Dalia, Chrysanthemum, and Zinnia), and Rubiaceac (e.g., coffee).

The present invention is effective against a wide variety of insect pests including the orders of Lepidoptera, Coleoptera, Diptera, Homoptera, Hemiptera, Thysanoptera, and Orthoptera. Examples of Lepidoptera include butterflies and moths. Coleoptera include beetles. Examples of Diptera are flies. Examples of Homoptera are aphids, whiteflies, scales, psyllids, leafhoppers, plant hoppers, cicadas, and treehoppers. The Hemiptera which are treatable in accordance with the present invention include true bugs. Thysanoptera which can be treated in accordance with the present invention include thrips. Examples of Orthoptera which can be treated in accordance with the present invention are grasshoppers, crickets, and katydids. Collectively, these orders of insect pests represent the most economically important group of pests for vegetable production worldwide.

The following examples are provided to illustrate embodiments of the present invention, but they are by no means intended to limit its scope.

EXAMPLES

Example 1

Isolation of boPI Gene from Cabbage

A cabbage (*Brassica oleracea* var. *capitala L* cv. Superpack) cDNA library was constructed in Lambda Zap II (Stratagene, LaJolla, Calif.) with mRNA purified from the young leaves of mature cabbage plants (Napoli et al., "Introduction of a Chimeric Chalcone Synthase Gene Into Petunia Results in Reversible Co-Suppression of Homologous Genes in trans," *Plant Cell* 2:279–289 (1990), which is hereby incorporated by reference in its entirety), shown previously to be a rich source of PI protein (Broadway et al., "Regulatory Mechanisms of Tryptic Inhibitory Activity in Cabbage Plants," *Phytochemistry* 29:3721–3725 (1990), which is hereby incorporated by reference in its entirety). This library was screened with antibodies produced in rabbits against affinity-purified cabbage PI (Broadway, "Purification and Partial Characterization of Trypsin/Chymotrypsin Inhibitors from Cabbage Foliage," *Phytochemistry* 33:21–27 (1993), which is hereby incorporated by reference in its entirety). Several positive clones were identified. An 809 bp clone ("pin 1–2") was plaque-purified and the insert sequenced using terminator cycle sequencing and an Applied Biosystems (Foster City, Calif.) fluorescence sequencer. The 809 bp *Brassica oleracea* proteinase inhibitor (bopi) coding region was isolated as an EcoRI-XhoI restriction fragment, then subcloned into pBluescript II SK (Stratagene, La Jolla, Calif.).

Example 2

Preparation of Vectors Containing bopi, Bt and *M. sexta* PIs

The bopi cDNA was isolated from pBluescript II SK by digestion with XbaI and XhoI to expose cohesive overhangs required for ligation into an intermediate cloning vector. The digested DNA was electrophoresed through a 0.8% agarose-TAE gel (50 mM Tris-HCL, 10 mM sodium acetate, 10 mM EDTA) and the DNA fragment corresponding to the *Brassica oleracea* proteinase inhibitor (BOPI) was removed from the gel using a razor blade. The DNA fragment was purified from the gel slice using the GeneClean® spin column (Bio101, Joshua, Calif.). The purified fragment was ligated into the shuttle vector, pBJ40, which had been precut with XbaI and XhoI restriction endonucleases. The pBJ40 vector is a plant vector that confers spectinomycin resistance (SpecR) in bacterial cells and contains the neomycin phosphotransferase II (NPT-II) gene that confers neomycin resistance in plant cells. The polylinker in pBJ40 is flanked by the cauliflower mosaic virus promoter (CaMV) 35S and nopaline synthase gene (nos) 3' terminator. The 2.2 Kb cassette was isolated as a SacI-EcoRI restriction fragment from pBJ40, and this was inserted between corresponding sites in the polylinker of the plant expression vector pBINI9. The plasmid, shown in FIG. 1, was renamed pBIN/BoPI. The plant transformation vectors containing *Bacillus thuringiensis* ("Bt") (Stewart et al., "Insect Control and Dosage Effects in Transgenic Canola, *Brassica Napus L.* (Brassicaceae), Containing a Synthetic *Bacillus thuringiensis* Cry Iac Gene," *Plant Physiol.* 112:115–120 (1996), which is hereby incorporated by reference in its entirety), and the *M. sexta* PIs (Thomas et al., "Introduction and Expression of an Insect Proteinase Inhibitor in Alfalfa (*Medicago Sativa L.*)" *Plant Cell Reports* 14:31–36 (1994), which is hereby incorporated by reference in its entirety), were of similar construction as BoPI, with the antibiosis transgenes under the control of the 35S promoter, and kanamycin as the plant selectable marker.

Purified DNA containing the intermediate construct was introduced into competent *E. coli* cells and grown on media containing spectinomycin for 18-hours at 37° C. Bacterial cells successfully transformed with the ligation mix formed individual colonies on the surface of the media. A single bacterial colony was then inoculated into liquid culture containing the appropriate antibiotic and grown overnight at 37° C. in a shaking incubator. The culture was transferred to a sterile 1.5 ml centrifuge tube and the cells were pelleted at 14,000 rpm for 3 minutes. The clarified supernatant was decanted and the bacterial pellet resuspended in 250 µl of cold resuspension buffer (50 mM Tris, 10 mM EDTA, pH 8.0). The cells were lysed in 250 µl of lysis buffer (200 mM NaOH, 1% SDS) for 5 minutes, then 250 µl of precipitation buffer (3.0 M potassium acetate, pH 5.5) was added. The cellular debris was pelleted by centrifugation at 14,000 rpm for 5 minutes and the supematant transferred to a fresh 1.5 µl centrifuge tube. Two volumes of cold 95% ethanol (EtOH) was added to precipitate the plasmid DNA and the tube spun at 14,000 rpm for 10 minutes to pellet the DNA. The supernatant was discarded and the pellet washed in 500 µl of cold 70% EtOH and centrifuged at 14,000 rpm for 5 minutes. The supernatant was discarded and the DNA pellet was allowed to dry for 30 minutes then resuspended in 25 µl of 1× TE buffer (10 mM Tris-HCl, pH 8.0, 1 mM EDTA). TE purified DNA was quantified by spectrophotometric analysis (260/280 nm) and restriction enzyme analysis to assess concentration and to ensure proper litigation and orientation of the inserted cDNA fragment in the shuttle vector.

Example 3

Transformation with boPI

The 2.2 Kb BoPI cassette was excised from the shuttle vector by digesting to completion with SacI, then partially digesting with EcoRI for 1 minute. TE DNA was electrophoresed through a 0.8% agarose TAE gel and the fragment corresponding to the BoPI cassette excised from the gel with a razor blade. The agarose was purified from the DNA fragment as previously described. The BoPI cassette was then ligated within the EcoRI and SacI restriction sites of the pBIN19 binary plan expression vector to produce pBIN19/BoPI, shown in FIG. 1. The modified pBIN 19 plant vector is a 10 Kb plasmid that uses the KanR selectable marker in both plant and bacterial transformants. The ligation mixture was transformed in to *E. coli* cells made competent for transformation and grown on selective media containing kanamycin at 37° C. for 18-hours. DNA from the resulting colonies was minipreped as previously described and analyzed by restriction analysis to confirm the presence of the BoPI cassette. The pBIN 19/BoPI was then mobilized into competent *Agrobacterium tumefaciens* for plant tissue culture.

Example 4

Characterization of bopi Gene

The bopi clone was 809 bp and contained the complete coding sequence as well as the complete 3' noncoding sequences, with an open reading frame (orf) of 642 bp starting at nucleotide 2. The amino acid residues at positions 22–41, shown in FIG. 2, correspond to the amino-terminal sequence determined for the most abundant mature PI. The predicted mature peptide had a calculated molecular weight of 21 kDa and a calculated pl of 4.94. These values fall within the range reported previously for cabbage PIs (Broadway, R. M., "Purification and Partial Characterization of Trypsin/Chymotrypsin Inhibitors from Cabbage Foliage," *Phytochemistry* 33:21–27 (1993), which is hereby incorporated by reference in its entirety).

Example 5

Characterization of the BoPI Peptide

Figure 2:
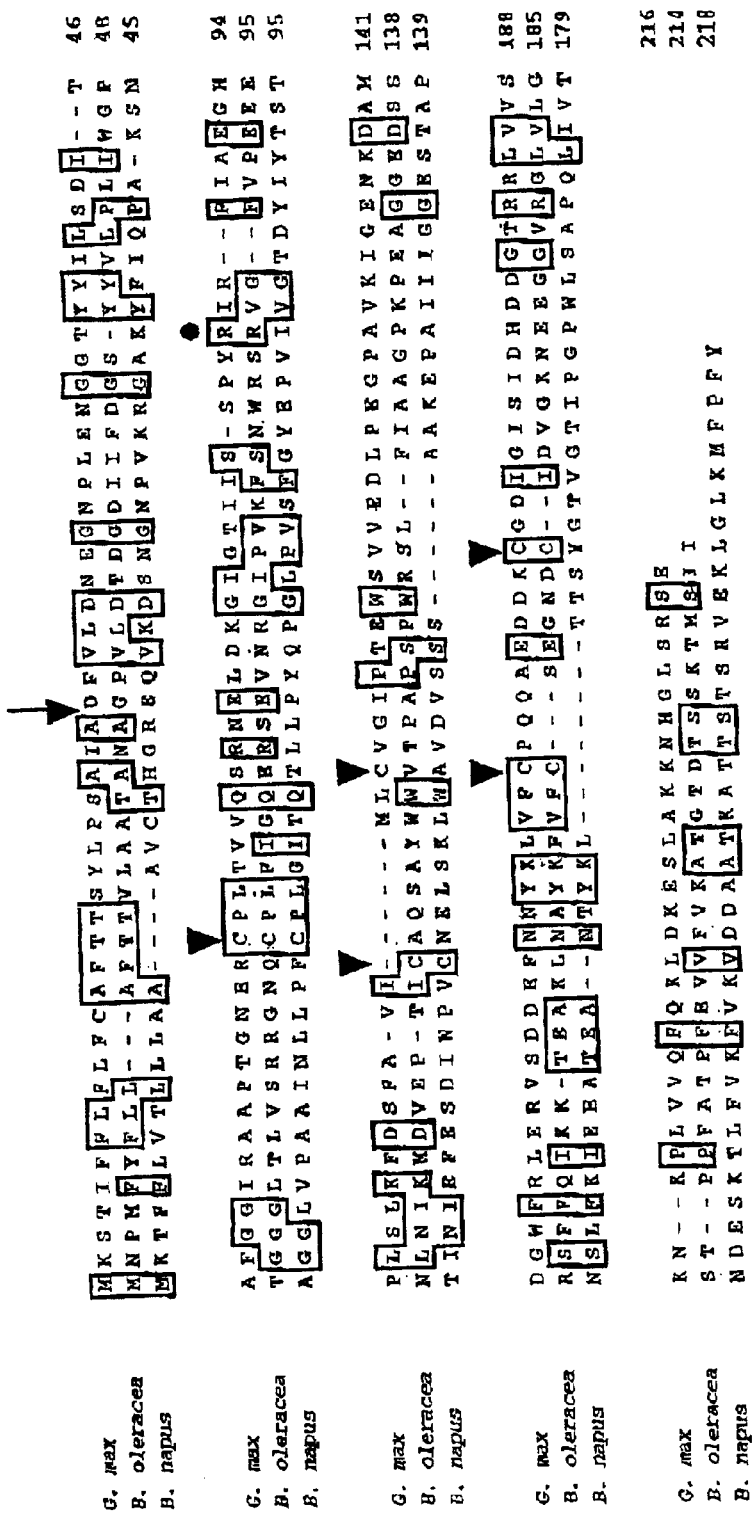
FIG. 2 is a comparison of the amino acid sequences derived from the bopi cDNA clone from cabbage (*B. oleracea*)(SEQ. ID. No. 2), a soybean Kunitz-type trypsin inhibitor 3 (*G. max*)(SEQ. ID. No. 3) and the drought-induced BnD22 from *B. napus* (SEQ. ID. No. 4). The active site arginines in the *B. oleracea* and *G. max* PIs are shown with a closed circle, conserved cysteine residues are shown with triangles and the cleavage site to produce the mature cabbage peptide is shown with a vertical arrow.

The pephide encoded by the clone (BoPI)(SEQ. ID. No. 2) was predicted to be a member of the soybean Kunitz class of trypsin inhibitors. It also showed significant similarity to the α-amylase/subtilisin inhibitors of cereals. The predicted peptide had a 30% identity to soybean trypsin inhibitor-3 (Jofuku et al., "Kunitz Trypsin Inhibitor Genes are Differentially Expressed During the Soybean Life cycle and In Transformed Tobacco Plants," *Plant Cell* 1: 1079–1093 (1989), which is hereby incorporated by reference in its entirety). The predicted BoPI peptide contained the amino acid sequence (SEQ. ID. No. 5) VLDTDGDIIFDGSYYVL at residues 24–40, which matched the signature pattern of (SEQ. ID. No. 6){LIVD}-x-D-x-{EDNTY}-{DG}-{RKHDENQ}-x-{LIVM}-x(5)-Y-x-{LIVM}) found in the amino-terminal section of Kunitz inhibitor family members (Bairoch, "PROSITE: A Dictionary of Sites and Patterns in Protein," *Nucleic Acids Res.* Apr. 25, 19 Suppl2247–9 (1991), which is hereby incorporated by reference in its entirety). This pattern is found starting at residues 27 and 23 for *G. max* and *B. napus*, respectively, shown in FIG. 2. The arginine residue at position 63 (as measured from the peptide cleavage site) corresponds to the active site arginine of soybean trypsin inhibitor (Sweet et al., "Crystal Structure of the Complex Porcine Trypsin with Soybean Trypsin Inhibitor"*Biochem*13: 4212–4228 (1974), which is hereby incorporated by reference in its entirety), and four cysteines that could facilitate intrachain disulfide bonds (Laskowski et al., "Protein Inhibitors of Proteinases," *Ann. Rev. Biochem*49: 593–626 (1980), which is hereby incorporated by reference in its entirety) are conserved in the cabbage sequence. A drought induced protein related to the Kunitz trypsin inhibitor family was cloned in *B. napus* (Downing et al., "A *Brassica napus* Transcript Encoding a Protein Related to the Kunitz Protease Inhibitor Family Accumulate Upon Water Stress in Leaves Not Seeds" *Plant J*. 2: 685–693 (1992), which is hereby incorporated by reference in its entirety). The conserved amino-terminal motif (residues 23–39) and the first cysteine pair is present in the *B. napus* sequence but not the active site arginine or the second cysteine pair, as shown in FIG. 2 (Downing et al., "A *Brassica napus* Transcript Encoding a Protein Related to the Kunitz Protease Inhibitor Family Accumulate Upon Water Stress in Leaves Not Seeds" *Plant J*. 2: 685–693 (1992), which is hereby incorporated by reference in its entirety). Overall, the predicted BoPI peptide had slightly less identity to the *B. napus* peptide (46/214 identical residues) compared to the soy peptide (56/214 identical residues).

Example 6

Cabbage pi Gene Family

Figure 3:
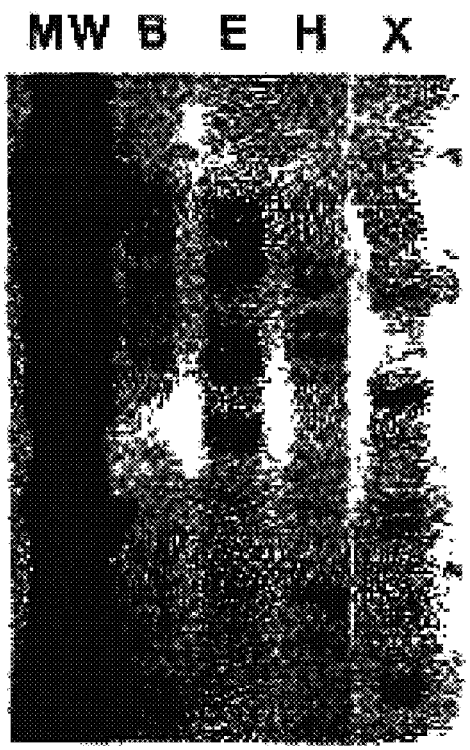
FIG. 3 shows a Southern blot analysis of cabbage genomic DNA digested with various restriction enzymes, then hybridized to digoxygenin-labeled cabbage pin 1–2. Lanes: MW, digoxygenin-UTP-tailed HindIII digest of lambda DNA (bands at 23, 9.4, 6.5, 4.4, 2.3, 2.0 and 0.56 kb) as standard; genomic fragments are shown in Lanes B (BamHI); E (EcoR);I; H (HindIII); X, (XbaI).

Genomic Southern blotting, shown in FIG. 3, and analysis of genomic clones suggested that BoPI was present as a member of a small gene family. This is similar to soybean (Jofuku et al., "Kunitz Trypsin Inhibitor Genes are Differentially Expressed During the Soybean Life Cycle and in Transformed Tobacco Plants," *Plant Cell* 1(11):1079–1093 (1989), which is hereby incorporated by reference in its entirety) and potato (Ishikawa et al., "A Family of Potato Genes That Encode Kunitz-type Proteinase Inhibitors: Structural Comparisons and Differential Expression," *Plant Cell Physiol*35(2):303–12 (1994), which is hereby incorporated by reference in its entirety), proteinase inhibitors and winged bean chymotrypsin inhibitor (Habu et al., "Structure and Regulated Expression of Kunitz Chymotrypsin Inhibitor Genes," *J. Biochem.* (Tokyo) 111(2):249–258 (1992), which is hereby incorporated by reference in its entirety) gene families. A cabbage genomic library in Lambda Fix II (Stratagene, La Jolla, Calif. was constructed and screened with a cabbage bopi 1–2 cDNA. Six positive clones were purified and shown to fall into 2 distinct classes by restriction digestion analysis. PCR amplification of the bopi coding sequences in the genomic clones suggested that these cabbage bopi genes are intronless. Cabbage genomic DNA was digested with enzymes that do not have sites in the bopi cDNA clone, and subsequently analyzed by Southern blotting. Several bands (6–8) of varying intensity were seen in each digest, as shown in FIG. 3.

Example 7

Transformation of Bacterial Cells with Binary Plant Expression Vector

Competent *Agrobacterium tumefaciens* (strain GV3850) cells were removed from −60° C. storage and 1–2 µg of purified pBJ40/BoPI DNA was pipetted directly into the 1.5 µl microfuge tube. The cells were allowed to thaw at 37° C. for 5 minutes and 1 ml of YEP broth was added. The cells were incubated at 28° C. for 1 hour, in a shaking incubator and using aseptic technique, 300 µl of the transformed GV3850 cells were pipetted onto YEP agar plates supplemented with the appropriate antibiotic(s). The plates were kept inverted for 2 days on an incubator preset to 20° C. DNA from successful transformation events resistant to antibiotic selection was purified by miniprep as described above, then verified by restriction analysis.

Example 8

Transgenic Plant Production

Seeds were sieved from desiccated pods of tobacco (*Nicotiana tabacum* cv Xanthi) using a fine mesh screen.

Approximately 100 mg (000 seeds) of seeds were placed into sterile 1.5 µl centrifuge tubes and 250 µl of water. The sterile water was decanted and the seeds allowed to dry under aseptic conditions overnight. The sterilized seeds were stored at 4° C.

Surface-sterilized tobacco seeds were germinated on media containing MS salts and grown under aseptic conditions until leaves formed (about 3–5 cm width). Seedlings were then transferred using aseptic technique to Magenta boxes containing MS salts and grown until the plants reached approximately 5–7 cm in height. Leaf disks approximately 0.5 cm in diameter were cut from these plants and transformed with *Agrobacterium tumefaciens* containing the pBfN19/BoPI plant expression vector. Leaf disks were co- cultivated on callus-inducing media without antibiotics for three days, then transferred to callus-inducing media containing antibiotics to select for transformants and to destroy any remaining Agrobacterium. Shoots from transgenic calli were transferred to media containing MS salts and the appropriate antibiotic and grown until the generation of roots. Rooting plants were transferred to nutrient supplemented soil and hardened off.

Primary transformants were grown in a growth chamber with 500 µE m$^{-2}$ s$^{-1}$ irradiance and 12-hr. photoperiods to maintain plants for insect bioassays. Plants were watered three times a week and fertilized as needed. Plant DNA was isolated according to published methods (Doyle et al., "A Rapid Isolation Procedure for Small Amounts of Fresh Leaf Tissue," *Phytochemical Bulletin* 19:11–15 (1987); Stewart et al., "A Rapid CTAB DNA Isolation Technique Usefuil for RAPD Fingerprinting and Other PCR Applications," *Bio-Techniques* 14:748–751 (1993), which are hereby incorporated by reference in its entirety). Plant DNA samples were quantified by fluorometric spectrophotometry (Hoefer DyNA Quant 200, Hoefer Pharmacia Biotech Inc, USA). PCR was used to assess transgenic state of the plants. PCR primers for each transgene and the expected PCR product (in bp) are shown in Table 1.

TABLE 1

| Gene & Primer(s) | Product (bp) | Primer (bp) | SEQ. ID. No. and Primer Sequence |
|---|---|---|---|
| BoPI | | | |
| Forward | 455 | 21mer | SEQ. ID. No. 7: GGCAGTTACTACGTTCTCCCC |
| Reverse | | 18mer | SEQ. ID. No. 8: CGATAGGGGTAGCGAATG |
| *M. sexta* PIs | | | |
| Forward | 770 | 20mer | SEQ. ID. No. 9 ACGACCAATTTACAGCCCAG |
| Reverse | | 23mer | SEQ. ID. No. 10: GTTGTACAAACGCTTCCCTCAGC |
| CrylAc | | | |
| Forward | 560 | 20mer | SEQ. ID. No. 11: ATTTGGGGAATCTTTGGTCC |
| Reverse | | 20mer | SEQ. ID. No. 12: ACAGTACGGATTGGGTAGCG |

*bp, Base pairs

Standard PCR was performed using 40 cycles of 94° C., 55° C., and 72° C. Ethidium bromide-stained agarose gel electrophoresis was used to visualize PCR products. Transgene expression or activity was estimated using protein blot analysis for Bt (Stewart et al., "Genetic Transformation, Recovery, and Characterization of Fertile Soybean Transgenic for a Synthetic *Bacillus Thuringiensis* CrylAc Gene," *Plant Physiol.* 112:121–129 (1996), which is hereby incorporated by reference in its entirety) or enzyme assays for PIs.

Multiple events of independently transformed lines containing each gene of interest were recovered from 300 leaf disks taken from an inbred cultivar of tobacco (Xanthi) transformed with Agrobacterium. This data is shown in Table 2.

TABLE 2

Transformation Efficiency of Tobacco Plants Subjected to Agrobacterium Mediated Gene Transfer.

| Transgene | Start[a] | Callus[b] | Shoots[c] | Rooted[d] | No of lines[e] |
|---|---|---|---|---|---|
| sBt | 300 | 137 (46%) | 50 | 38 (76%) | 21 |
| *M. sexta* AE | 300 | 126 (42%) | 50 | 28 (56%) | 18 |
| *M. sexta* AC | 300 | 87 (29%) | 50 | 30 (60%) | 20 |
| *M. sexta* AT | 300 | 95 (32%) | 50 | 23 (46%) | 13 |
| BoPi | 300 | 131 (44%) | 50 | 46 (92%) | 14 |

[a]Number of leaf disks co-cultivated in Agrobacterium.
[b]Number of leaf disks that produced callus during antibiotic selection.
[c]Total number of shoots excised from callus.
[d]Number of rooted shoots, each representing unique transgenic events.

All plants were morphologically normal and fertile. Southern blot analysis demonstrated that all transgenes were integrated with 1–4 copies contained in plants.

Example 9

Enzyme Activity and Transgene Expression

The initial enzyme assays performed on bulk numbers of transgenic plants were performed as follows. Trypsin, chymotrypsin or elastase inhibition activity in transgenic plants was determined by a modification of the methods described by Geiger et al., "Determination of Trypsin Inhibition," in Bergmeyer, eds., *Methods of Enzymatic Analysis HU B*, Deerfield Beach, Fla.: VCH Publishers, pp. 121–126 (1983), which is hereby incorporated by reference in its entirety. Approximately 0.5 gm of fresh leaf tissue was homogenized in 5 ml of cold extraction buffer (25 mM NaHPO4 pH 7.0, 10 mM EDTA free acid, 1% Sarkosyl, 1% Triton-X 100). Each homogenate was poured into a sterile, 50-ml conical centrifuge tube and diluted with an additional 20 ml of extraction buffer. A portion of each extract was used in a Bradford analysis (BioRad, USA) to determine the total soluble protein concentration. Each sample was assayed in quadruplicate by combining 100 µg of total plant protein and the appropriate amount of extraction buffer to bring each reaction volume to 800 µl in a 1 ml quartz cuvette. After briefly mixing the reaction mixtures, 200 µl of BAPNA (1.74 mg ml$^{-1}$)(N α-benzoyl-DL-arginine p-nitroanilide, Sigma, St. Louis, Mo.) was mixed into each sample. A standard containing 2.5 mg/ml bovine trypsin (or chymotrypsin or elastase, as appropriate) and a blank solution lacking the BAPNA substrate were prepared to accompany each set of plant samples. All cuvettes were incubated at 25° C. for 10 min. after the addition of all reagents. The absorbance of each sample was recorded by spectrophotometry at 410 nm using the substrate blank and the standard as a reference. The resulting spectrophotometric data were used to calculate the percent inhibition of each PI/plant sample.

Subsequent enzyme assays from an improved procedure (Menges et al., "Continuous Assay of Proteases Using a Microtiter Plate Fluorescence Reader," *Anal. Biochem.* 254:144–147 (1997); and Thompson et al., "A BODIPY Fluorescent Microplate Assay for Measuring Activity of Calpains and Other Proteases," *Anal. Biochem.* 279:170–178 (2000), which are hereby incorporated by reference in its entirety) were performed on leaves extracts from individual plants. Approximately 2 gm of fresh leaf tissue was macerated in 2 ml of homogenization buffer (100 mM Tris-HCl pH 7.5, 0.1 M $CaCl_2$) using a semi-automated plant tissue homogenizer. The homogenate was transferred to a clean 1.5 ml centrifuge tube and clarified by centrifugation at 15,000 rpm, 4° C. for 10 minutes. Total protein of each plant extract was assessed by BCA assay (Pierce, USA). For inhibition assays, 10 mg/ml working stocks of trypsin and trypsin-chymotrypsin protease inhibitor (Sigma Chemical Co., St. Louis, Mo.) were prepared by dissolving each compound in digestion buffer (10 mM Tris-HCl, pH 7.8, containing 0.1 mM sodium azide).

Protease activity was determined using a fluorescence-based assay (EnzChek BODIPY Fluorescence Kit, Molecular Probes, USA) in a 96-well format. Assays were carried out in duplicate and blanks were used to account for any background. A standard curve was generated to determine the activity of purified protease, and to determine the effect of varying levels of purified inhibitor on a known concentration of protease. To detect protease-inhibitor activity in the plant extracts, 25 µg of soluble protein was loaded into the well of a flat bottom, black 96-well plate (Costar, USA). Enough trypsin was added to each sample so that a final concentration of 2.5 µg/ml would be achieved. Enough digestion buffer was added to each sample to bring the volume to 100 µl. Finally, 100 µl of the BIODIPY casein working solution was added. The microplate was incubated for 1 hour at room temperature, protected from light. Fluorescence was measured with a filter fluorometer (excitation 485 nm, emission 535 nm) on a SpectraFluor Plus microplate multi-detection plate reader controlled by X-Flor acquisition utility software (TECAN Instruments, USA).

Bt transgenic plants had similar expression levels compared with earlier work with transgenic canola (Stewart et al., "Insect Control and Dosage Effects in Transgenic Canola, *Brassica napus* L. (Brassicaceae), Containing a Synthetic *Bacillus thuringiensis cry* IAc Gene," *Plant Physiol.* 112:115–120 (996), which is hereby incorporated by reference in its entirety). There was a range of low (0.005%) to high (0.1%) expression levels in transgenic plants. Likewise, enzyme analysis of PI transgenics showed a range of expression as determined by the hydrolysis of BApNA by the appropriate digestive enzyme. For example, BoPI transgenic plants (n=11) inhibited the release of p-nitroaniline from 6.31% to 27.61% compared to wild-type plants. There were no significant differences in proteinase inhibition among PIs at the P=0.05 level. In the subsequent enzyme assays to more accurately assess individual plant line differences using an improved method (Menges et al., "Continuous Assay of Proteases Using a Microtiter Plate Fluorescence Reader," *Anal. Biochem.* 254:144–147 (1997); and Thompson et al., "A BODIPY Fluorescent Microplate Assay for Measuring Activity of Calpains and Other Proteases," *Anal. Biochem.* 279:170–178 (2000), which are hereby incorporated by reference in its entirety), the relative patterns of transgenic expressed PI to endogenous PI were similar. However, there was great variation among lines of all transgenic plants' expression of the transgenes, as well as endogenous PI. FIG. 4 shows the results of trypsin inhibition assays performed on wildtype tobacco (Xanthi), BoPI and *Manduca sexta* antitrypsin (VK32) (individual events) for transgenic T1 progeny.

Example 10

Insect Bioassays of Transgenic Plants

Bioassay arenas were constructed using a 100-mm×10-nmm polystyrene petri dish. A single 10-cm diameter filter paper was placed in the bottom of the dish then moistened with 1–2 ml of deionized water. Leaf disks were cut from mature tobacco leaves using a 4-cm diameter leaf borer with a beveled cutting edge that was fashioned from a length of copper pipe. Two leaf disks from each plant were placed on the filter paper, then the arena was covered using the lid of the petri dish. Three replicates for each plant line were prepared.

The lepidopteran species used in this experiment were the *Bacillus thuringiensis* (Bt) susceptible tobacco budworm (*Heliothis virescens*)(strain YDK), the Bt-resistant tobacco budworm (strain YHD2) (Gould et al., "Selection and Genetic Analysis of a *Heliothis Virescens* (Lepidoptera:Noctuidae) Strain with High Levels of Resistance to *Bacillus Thuringiensis* Toxins," *J. Econ. Entomol.*88:1545–1559 (1995), which is hereby incorporated by reference in its entirety), and corn earworm (*Helicoverpa zea*). The eggs of each insect strain were incubated in 30-ml transparent plastic cups with unwaxed cardboard lids at 20° C. until they hatched. Three newly hatched larvae were removed from the plastic cups and applied to each leaf disk in a bioassay arena using a fine hair paint brush, and the lid placed back on the bioassay arena. The bioassays were maintained on a stainless steel wire shelf that allowed even air circulation, and the bioassays were conducted for five days, with periodic watering of the disks to maintain the health of the leaf disks. The treatments were maintained at 25° C. and constantly illuminated with fluorescent lighting throughout the experiment. Data were collected at the conclusion of each trial measuring the antibiosis parameters: percent mortality, body length of surviving insects, and defoliation of the leaf disks. The data were analyzed using SAS. A two-way analysis of variance (ANOVA) was performed using the categorical variables transgenic plant type and insect species to determine any significant differences with respect to the antibiosis parameters. Multiple comparisons using Tukey's studentized range test were performed on all main effect means.

The growth and defoliation by the insects on wild-type (WT) leaf disks, shown in FIG. 5 and FIG. 6, respectively, was generally higher than transgenic leaf disks for all three insects ($P<0.05$). Likewise, as shown in FIG. 7, larval corn earworm (CEW) survived significantly better on WT leaves than on any of the transgenics. As seen in FIG. 7, all CEW that fed on transgenic tobacco expressing the Bt endotoxin were killed. However, there was more survivorship of CEW when fed on tobacco expressing PI proteins compared with Bt. Survivorship of CEW on plants expressing PI proteins (BoPI, M. sexta-AT, AC and AE) was similar. Survivorship of CEW on Bt transgenic plants was significantly different than CEW on PI transgenic plants ($P<0.05$).

FIG. 7 shows a low, but comparable level of survivorship in YHD2 insects on Bt and BoPI plants. However, survivorship was high for YHD2 on plants expressing the *M. sexta* derived PIs. Moreover, the survivorship of YHD2 that fed on plants expressing the *M. sexta* PIs (AT, AC, and AE) was similar to that of YHD2 on wild-type plants. The mortality of YHD2 observed in Bt and BoPI transgenics was significantly different than the survivorship of YHD2 observed in the *M. sexta* derived PI transgenics ($P<0.05$). This trend was also observed in the YDK strain of *H. virescens*. Both Bt and BoPI transgenics were associated with similar levels of mortality of YDK insects. However, survivorship of YDK insects on any *M. sexta* transgenic plant showed survivability similar to YDK on WT plants. The survival of YDK on Bt and BoPI transgenic plants was similar, and the values were significantly lower than the survivorship of YDK on any of the *M. sexta* derived PI transgenics (P<0.05).

Figure 6:
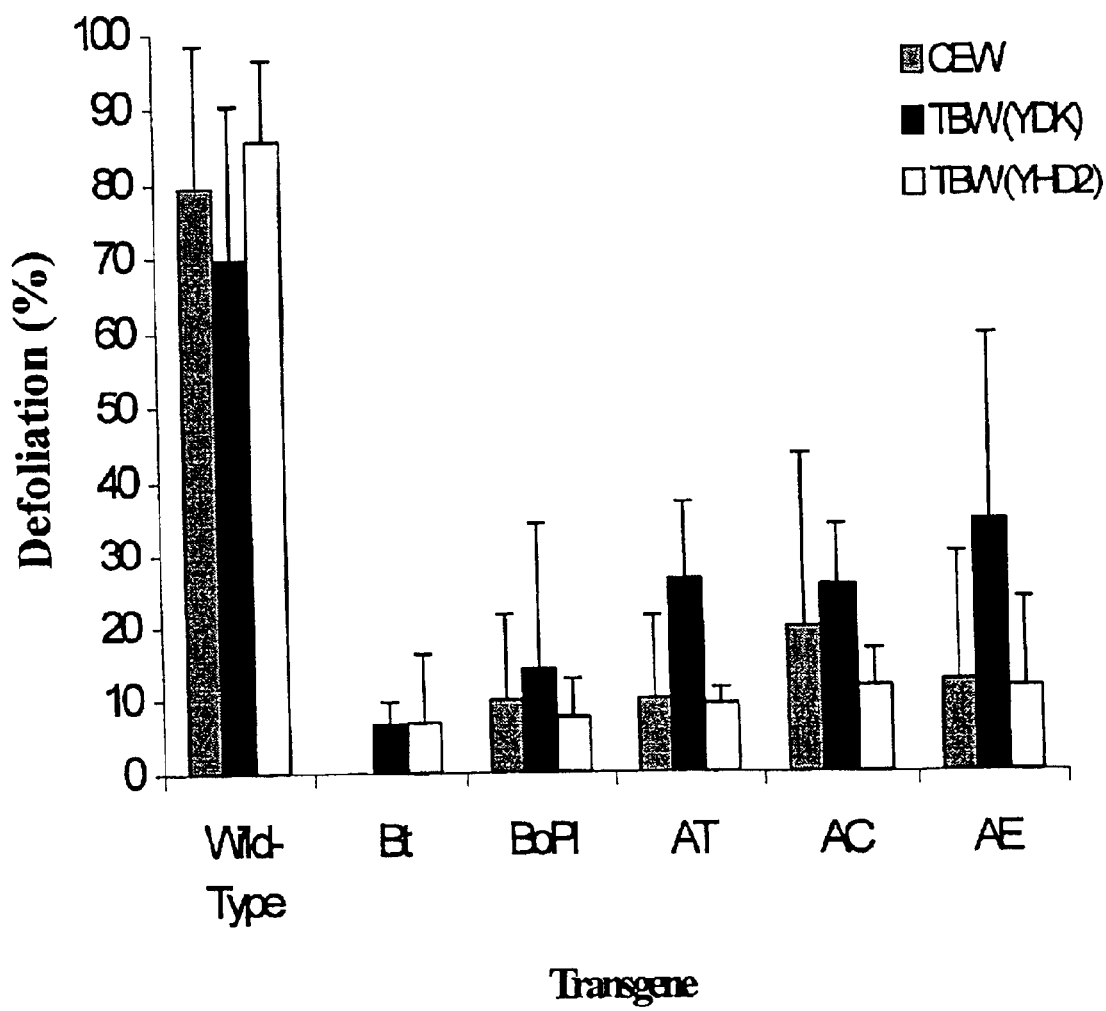
FIG. 6 shows the percent defoliation resulting from corn earworm (CEW)(*Helicoverpa zea*) and tobacco budworm (TBW)(*Heliothis virescens*) which is either Bt-susceptible (YDK), or Bt-resistant (YHD2), when feeding on leaf discs from wild-type tobacco; *Bacillus thuringiensis* (Bt); *Brassica oleracea* PI (BoPI) and *Manduca sexta* anti-trypsin (AT), anti-chymotrypsin (AC) and anti-elastase (AE) PI transgenic tobacco.

As anticipated, and shown in FIG. 6, the average defoliation by CEW, YDK, and YHD2 on wild-type plants was significantly higher than the defoliation observed on the transgenic plants. The average defoliation by CEW in all transgenics was similar, and no significant differences in defoliation by CEW were observed among transgene type. However, defoliation by CEW was slightly higher among plants expressing proteinase inhibitors than in Bt plants. Likewise, the average defoliation by YHD2 in all transgenics was similar, and no significant differences were observed among transgene type. Defoliation by YHD2 was slightly higher among plants expressing proteinase inhibitors than in Bt plants. Defoliation by YDK in plants expressing the *M. sexta* AT and AE proteinase inhibitor proteins had defoliation levels similar to non-transgenic plants. There were no differences in the average defoliation by YDK on Bt, BoPI and the *M. sexta* AC transgenics.

Figure 5:
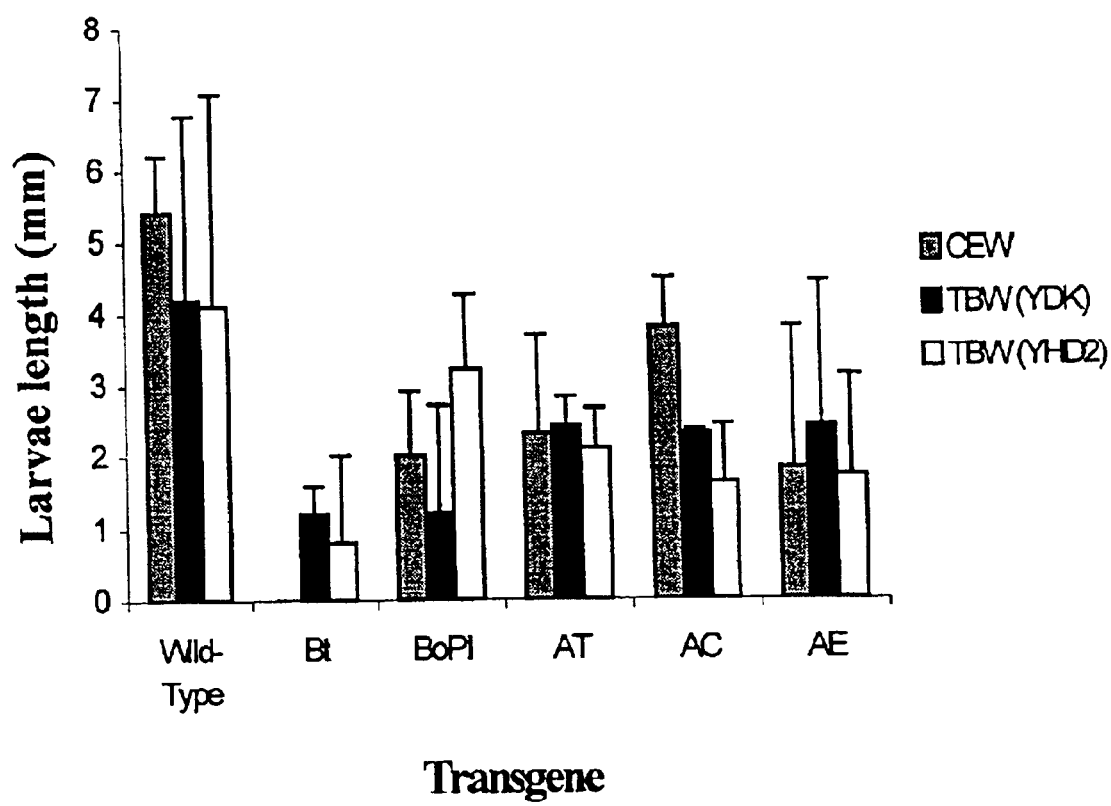
FIG. 5 shows the growth (as measured by larval length)of corn earworm (CEW)(*Helicoverpa zea*) and tobacco budworm (TBW)(*Heliothis virescens*) which is either Bt-susceptible (YDK), or Bt-resistant (YHD2), when feeding on leaf discs from wild-type tobacco; *Bacillus thuringiensis* (Bt); *Brassica oleracea* PI (BoPI), and *Manduca sexta* anti-trypsin (AT), anti-chymotrypsin (AC) and anti-elastase (AE) PI transgenic tobacco.

The average length of CEW on Bt plants was smaller than CEW on any plant expressing a proteinase inhibitor protein, as shown in FIG. 5. The average length of H. virescens (YDK and YHD2) on Bt and BoPI plants were similar. These insects were smaller than *H. virescens* on the plants expressing the *M. sexta* proteinase inhibitors. However, the means observed between Bt and BoPI versus the *M. sexta* PIs were not significantly different.

Previous studies have shown a significant reduction in the growth and development of caterpillars on plants transformed with Bt or PI (Hoffmann et al., "Field Evaluation of Transgenic Tobacco Containing Genes Encoding *Bacillus Thuringiensis* Delta-Endotoxin or Cowpea Trypsin Inhibitor: Efficacy Against *Heliocoverpa zea* (Lepidoptera: Noctuidae)," *J. Econ. Entomol.*85:2516–2522 (1992); Hua et al., "Transgenic Tobacco Plants by Cotransformnation With Proteinase Inhibitor II and Delta-Endotoxin Genes," *Chinese Science Bulletin* 38:1561–1566 (1993); Macintosh et al., "Potentiation of *Bacillus thuringiensis* Insecticidal Activity by Serine Protease Inhibitors," *J. Agric. Food Chem.* 38:1145–1152 (1990); Santos et al., "Testing Trangenes for Insect Resistance Using Arabidopsis," *Molecular Breeding* 3:183–194 (1997), which are hereby incorporated by reference in its entirety). As seen in FIG. 5, the average length of CEW on Bt plants was smaller than CEW on any plant expressing a proteinase inhibitor protein. The average length of *H. virescens* (YDK and YHD2) on Bt and BoPI plants were similar. These insects were smaller than *H. virescens* on the plants expressing the *M. sexta* proteinase inhibitors.

Figure 7:
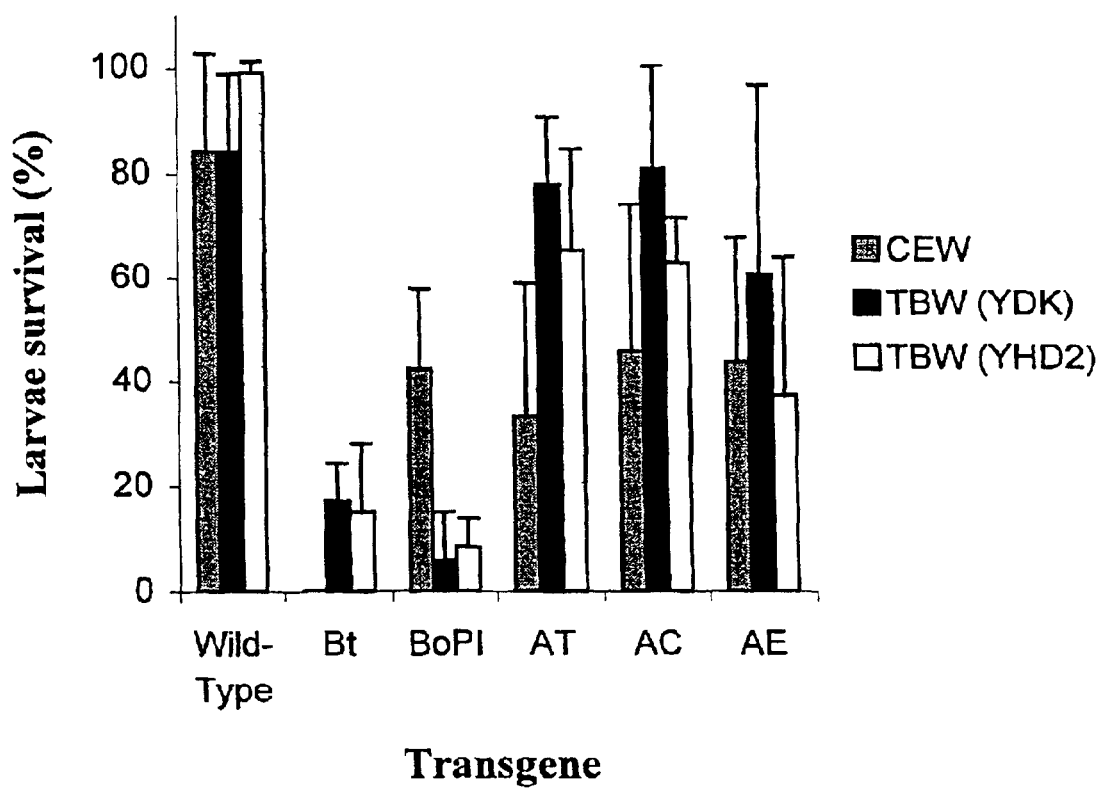
FIG. 7 shows percent larval survival of corn earworm (CEW) (*Helicoverpa zea*) and tobacco budworm (TBW) (*Heliothis virescens*) which is either Bt-susceptible (YDK), or Bt-resistant (YHD2), when feeding on leaf discs from wild-type tobacco; *Bacillus thuringiensis* (Bt); *Brassica oleracea* PI (BoPI) and *Manduca sexta* anti-trypsin (AT), anti-chymotrypsin (AC) and anti-elastase (AE) PI transgenic tobacco.

As shown in FIG. 7, tobacco transformed with Br Cryl Ac endotoxin was more effective in killing insects than any of the PIs examined herein, with the exception of BoPI on TBW survivorship in the bioassay. This profound difference between Bt and the PIs can be attributed to mode of action. The effect of Bt ingestion is immediate and more lethal than that of the PIs. Ingestion of the Bt endotoxin induces pore formation in the cells in the insect midgut, causing death within hours. In contrast, ingestion of PIs will ultimately lead to a decline in the feeding behavior of the insects, resulting in a decrease in growth, causing death in several days.

The cabbage-derived PI (BOPI) used in the present invention shows promise as a useful natural insecticide against certain lepidopteran insects. BoPI effectively reduced survivorship of the Bt-resistant (YHD2) and Bt-susceptible (YDK) strains of tobacco budworm, exhibiting levels similar to plants producing the Cryl Ac toxin. However, BoPI plants were not as effective at reducing survivorship of corn earworn (CEW). This finding is consistent with a previous study on CEW that incorporated cabbage proteinase inhibitors into artificial diets (Broadway, "Are Insects Resistant to Plant Proteinase Inhibitors?," *J. Insect Physiol.* 41:107–116 (1995); and Broadway, "Dietary Proteinase Inhibitors Alter Complement of Midgut Proteases," *Arch. Insect Biochem. Physiol.* 32:39–53 (1996), which are hereby incorporated by reference in its entirety). Broadway investigated the potential of herbivorous insects to become resistant to plant proteinase inhibitors, under the hypothesis that long-term exposure to certain proteinase inhibitors would reduce the toxic effects of subsequent exposure to those toxins. For instance, diamondback moth (*Plutella xylostella*), imported cabbageworm (*Pieris rapae*), and cabbage loopers (*Trichoplusia ni*) are all cabbage specialists, and possess adaptive defenses to cabbage phytochemicals. Hypothetically, they should be more resistant to PIs in cabbage. In contrast, generalists like CEW, an insect that does not feed on cabbage, should be more susceptible to cabbage PIs. In vitro inhibition studies demonstrated that the trypsins from imported cabbageworm were not susceptible to inhibition by cabbage PI, while the trypsins from CEW were significantly inhibited by cabbage PI (supporting the hypothesis). However, feeding studies using artificial diet demonstrated that, growth and development for both species was not effected by ingestion of cabbage PI (Broadway, "Are Insects Resistant to Plant Proteinase Inhibitors?," *J. Insect Physiol.* 41:107–116 (1995), which is hereby incorporated by reference in its entirety). Similar results were found when the insects were feeding on plant tissue containing trypsin inhibitors (Broadway et al., "Influence of Cabbage Proteinase Inhibitors in situ on the Growth of Larval *Trichoplusia ni* and *Pieris rapae,*" *Journal of Chemical Ecology* 18:1009–1023 (1992); and Broadway, "Are Insects Resistant to Plant Proteinase Inhibitors?," *J. Insect Physiol.* 41:107–116 (1995), which are hereby incorporated by reference in its entirety). In contrast, the cabbage looper was susceptible to cabbage PI as demonstrated by in vitro inhibition studies and ingestion studies, demonstrating that some lepidopterans have the ability to adapt to certain Pls by secreting a suite of enzymes that are not susceptible to those inhibitors (Broadway, "Dietary Proteinase Inhibitors Alter Complement of Midgut Proteases," *Arch. Insect Biochem. Physiol.* 32:39–53 (1996), which is hereby incorporated by reference in its entirety). As shown in FIGS. 5 and 6, respectively, defoliation and survivorship levels by corn earworm on BoPI plants were similar to those observed in plants expressing the *Manduca sexta* derived serine Pls, confirming that CEW is not susceptible to cabbage PI.

Figure 4:
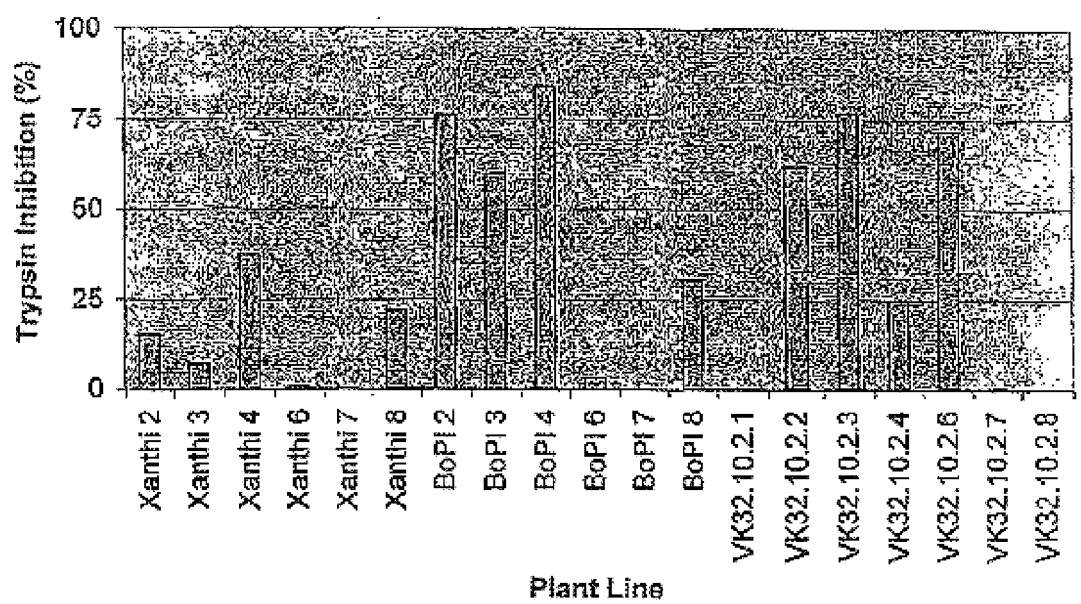
FIG. 4 shows results of enzyme assays performed on wildtype tobacco (Xanthi), BoPI and *Manduca sexta* anti-chymotrypsin (VK32) (individual events) for transgenic TI progeny.

FIGS. 4, 5, and 6 show heightened sensitivity to Bt on the part of CEW. It is not clear why CEW was completely controlled in this study by Cry 1 Ac. Since a range of Bt expression was observed, some larval survival was expected. Previous investigations have reported that CEW was less sensitive to the Cry 1 Ac delta-endotoxin than the data herein indicates (Luttrell et al., "Variation in Susceptibility of Noctuid (Lepidoptera) Larvae Attacking Cotton and Soybean to Purified Endotoxin Proteins and Commercial Formulations of *Bacillus thuringiensis,*"*J. Econ. Entomol.* 92:21–32 (1999); Macintosh et al., "Specificity and Efficacy of Purified *Bacillus thuringiensis* Proteins Against Agronomically Important Insects," *J. Invertebr. Pathol.* 56:258–266 (1990); and Sims et al., "Field Evaluation of Transgenic Corn Containing a *Bacillus thuringiensis* Berliner Insecticidal Protein Gene Against *Helicoverpa zea*

(Lepidoptera: Noctuidae)," *J. Entomol. Sci.* 31:340–346 (1996), which are hereby incorporated by reference in its entirety). One group reported significant differences in the susceptibility to Bt (Cry 1 Ac) among field strains of TBW and CEW (Stone et al., "Geographic Susceptibility of *Heliothis virescens* and *Heliocoverpa zea* (Lepidoptera:Noctuidae) to *Bacillus thuringiensis,*" *J. Econ. Entomol.* 84:989–994 (1993), which is hereby incorporated by reference in its entirety). Of the two species, CEW had a higher tolerance for Cry 1 Ac. It was also unusual to observe that there were no differences in performance between TDK and YHD2 when allowed to feed on Bt-transgenic plants. While no explanation is currently available for these apparently aberrant results, the BoPI transgenic plants performed comparably to Bt in TBW control. Thus, the present invention may have more widespread application than previous data would predicate. Furthermore, BoPI may well prove to be an effective PI for lepidopteran control in transgenic plants when Bt is not desirable. It might also be useful when a plant-derived transgene is desired.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A nucleic acid construct comprising:
    a nucleic acid molecule that encodes a Kuntz-type serine proteinase inhibitor, wherein the nucleic acid molecule either: (a) has the nucleotide sequence of SEQ ID NO: 1 or (b) encodes a protein having the amino acid sequence of SEQ ID NO: 2;
    an operably linked heterologous DNA promoter; and
    an operably linked 3' regulatory region.

2. An expression system comprising the nucleic acid construct according to claim 1.

3. A host cell transformed with thle nucleic acid construct according to claim 1.

4. The host cell according to claim 3, wherein the host cell is selected from the group consisting of a bacterial cell, a virus, a yeast cell and a plant cell.

5. The host cell according to claim 4, wherein the host cell is a plant cell.

6. The host cell according to claim 4, wherein the host cell is a bacterial cell.

7. A transgenic plant transformed with the nucleic acid construct according to claim 1.

8. The transgenic plant according to claim 7, wherein the plant is selected from the group consisting of Gramineae, Liliaceae, Iridaceae, Orchidaceae, Salicaceae, Ranunculaceae, Magnoliaceae, Cruciferae, Rosaceae, Leguminosae, Malvaceae, Umbelliferae, Labitatae, Solanaceae, Cucurbitaceae, Comnpositae, and Rubiaceae.

9. A transgenic plant seed transformed with the nucleic acid construct according to claim 1.

10. The transgenic plant seed according to claim 9, wherein the seed from a plant selected from the group consisting of Gramineae, Liliaceae, Iridaceae, Orchidaceae, Salicaceae, Ranunculaceae, Magnoliaceae, Cruciferae, Rosaceae, Leguminosae, Malvaceae, Umbelliferae, Labitatae, Solaaaceae, Cucurbitaceae, Compositae, and Rubiaoceae.

11. A method for conferring resistance to insects to a plant or plant seed comprising:
    transforming a plant or plant seed with the nucleic acid construct according to claim 1; and growing the transformed plant or plant seed under conditions effective to impart resistance to insects.

12. A transgenic plant produced by the method according to claim 11.

13. A transgenic plant seed oroduced by the method according to claim 11.

14. The method according to claim 11, wherein the insects are selected from the group consisting of Lepidoptera, Coleoptera, Diptera, Homoptera, Hemiptera, Thysanoptera, and Orthoptera.

15. The method according to claim 11, wherein the insects are *Heliothis viresens* or *Heliocoverpa zea*.

16. The method according to claim 11, wherein the transgenic plant is selected from a group consisting of Grarnineae, Liliaceae, iridaceae, Orchidaceac, Salicaceae, Ramunculaceae, Magnoliaccae, Cruciferae, Rosaceae, Leguminiosae, Malvaceae, Umbelliferae, Labitatae, Solanaceae, Cucurbitaceae, Compositae, and Rubiaceae.

* * * * *